United States Patent
Schuler et al.

(10) Patent No.: US 8,656,930 B2
(45) Date of Patent: *Feb. 25, 2014

(54) METHOD AND SYSTEM FOR PROCESSING CANCER CELL ELECTRICAL SIGNALS FOR MEDICAL THERAPY

(75) Inventors: Eleanor L. Schuler, Rio Rancho, NM (US); James K. Poliner, Bernallilo, NM (US); Donald E. Nash, Albuquerque, NM (US)

(73) Assignee: Neuro-Code Tech Holdings, LLC, Albuquerque, NM (US)

( * ) Notice: Subject to any disclaimer, the term of this patent is extended or adjusted under 35 U.S.C. 154(b) by 873 days.

This patent is subject to a terminal disclaimer.

(21) Appl. No.: 12/812,576

(22) PCT Filed: Jan. 12, 2009

(86) PCT No.: PCT/US2009/030701
§ 371 (c)(1),
(2), (4) Date: Jul. 12, 2010

(87) PCT Pub. No.: WO2009/089517
PCT Pub. Date: Jul. 16, 2009

(65) Prior Publication Data
US 2010/0286689 A1 Nov. 11, 2010

Related U.S. Application Data

(60) Provisional application No. 61/020,271, filed on Jan. 10, 2008.

(51) Int. Cl.
*A61B 19/00* (2006.01)
(52) U.S. Cl.
USPC ............................................ 128/898; 606/33

(58) Field of Classification Search
USPC ........... 606/32–34; 607/98, 99; 600/9, 12–14; 128/898
See application file for complete search history.

(56) References Cited

U.S. PATENT DOCUMENTS

| | | | |
|---|---|---|---|
| 5,610,136 A * | 3/1997 | McMichael | 514/9.7 |
| 7,160,239 B2 * | 1/2007 | Ichikawa et al. | 600/9 |
| 2004/0072731 A1 * | 4/2004 | McMichael | 514/8 |
| 2006/0121590 A1 * | 6/2006 | Speerli | 435/173.1 |
| 2009/0232740 A1 * | 9/2009 | Rishpon et al. | 424/9.2 |
| 2010/0016651 A1 * | 1/2010 | Sivo | 600/14 |
| 2010/0233021 A1 * | 9/2010 | Sliwa et al. | 422/20 |
| 2012/0184800 A1 * | 7/2012 | Brighton | 600/13 |
| 2013/0261711 A1 * | 10/2013 | Sivo | 607/103 |

OTHER PUBLICATIONS

Nucciitelli et al. "Nanosecond pulsed electric fields cause melanomas to self-destruct." Biochemical and Biophysical Research Communications 343 (2006) 351-360.*

* cited by examiner

*Primary Examiner* — Ahmed Farah
(74) *Attorney, Agent, or Firm* — Kermit D. Lopez; Luis M. Ortiz; Ortiz & Lopez, PLLC

(57) ABSTRACT

A scientific computer system with processor capable of recording, storing and reprogramming the natural electrical signals of cancer cells as found in tumors of humans and animals. The reprogramming process is designed to create a confounding electrical signal for retransmission into a malignant tumor to damage or shut-down the cellular internal electrical communication system. Altering the electrical charge on the glycocalyx of the outer cell membrane is also part of the treatment by application of ions. The invention causes cancer cell death as a medical treatment using ultra-low voltage and amperage encoded signals which are reprogrammed from cancer cell communication signals.

11 Claims, 1 Drawing Sheet

METHOD AND SYSTEM FOR PROCESSING CANCER CELL ELECTRICAL SIGNALS FOR MEDICAL THERAPY

RELATED APPLICATION

This application is the U.S. national phase filing of International Patent Application No. PCT/US2009/030701 having an international filing date of Jan. 12, 2009 and which claims priority from U.S. Provisional Patent Application Ser. No. 61/020,271 filed Jan. 10, 2008.

TECHNICAL FIELD

The present invention relates to the medical therapy of cancers throughout the entire human or animal body. Most particularly, the invention relates to an all analog computer system or a hybrid analog-digital computer system for receiving and recording the intrinsic electrical signals of individual cancer cells or the electrical signature of clusters of malignant cancer cells. The signals are recorded and entered into the computer system for analysis and reprogramming into treatment signals. The treatment signals are transmitted or broadcast into malignant tumors as a means to shut down or damage the cellular-based electrical system to destroy the cancer. A tumor may require multiple treatments to insure that the malignant cellular cluster is entirely treated.

BACKGROUND OF THE INVENTION

Every biological process is also an electrical process. All living cells, including cancer cells, have electrical capability and can communicate internally to processes within the cell as well as with adjacent cells. Many different cells are able to participate in long distance communication both within and outside the body.

Progress in archeology, paleontology, biology, geology and many other scientific and engineering specialties have contributed to an understanding of prehistory and the nature of early cellular life. Particularly, scientific publications have contributed greatly to being able grasp how the world has progressed from the earliest times and how this relates to modern times. Carbon isotope and argon dating technologies and the studies of unearthed findings and evidence from pre-historical times have contributed to knowledge about the progress of cellular life.

Modern neuroscience, cell biology and microscopy along with the medical sciences have steadily examined the anatomy and physiological characteristics of cells and have richly added to the published body of knowledge regarding those very interesting tiny examples of life. Genetic and embryology have provided interesting information on how cells came to organize themselves into efficient and complex creatures and beings. Yet everything is far from being known regarding the science and capability of individual cellular communication and how nerve networks play a part in keeping everything operationally coordinated.

Humans and animals are constructed entirely of definable cells and as such are identified as multi-cellular organisms. Accepted cell theory maintains that the cell is the fundamental organizational unit of life and that all living things are composed of cells. About 100 trillion cells are composed in the human body to construct the shape, function and to conduct all life and operational purposes. Every cell in any living human or animal is part of a massive and complex biological process. The cells perform a wide variety of tasks for which they are individually designed and serve in harmony with a great compendium of unique and highly specialized but flexible purpose. There are cells that help excrete chemicals, move muscles, circulate blood and nutrients, operate vital organs and serve as bones and tendons. Eyes, ears, tongue, skin, glands and many other body parts all are composed of a wide variety of different and specialized kinds of cells.

Normal cells have electro-chemical processes within their surrounding plasma membranes which are the outer limit of the cell proper. Within their individual plasma membranes are components of the internal cell which consists of processes that operate the electro-chemical mechanisms that allow cell functions to be maintained. Cells have to obtain nutrition and be able to reproduce, defend and repair themself as well as perform the primary purpose for which they are designed for. For example, cells working in teams may produce adrenalin or insulin or participate in causing a heart to beat or process food within the digestive tract. Individual cells have a cytoskeleton to serve as support to maintain cell shape and to provide spaces or compartments in which chemical and electrical processes can be conducted.

There are many kinds of cells, each specialized to fulfill specific duties and functions. Cells are small—a pencil dot might be the space occupied by 60 to 500 cells. Cancer cells can exist as small-cell or large-cell varieties and can form tumors of great variation in size. Normal cells are of different size depending on the kind of mechanisms that are enclosed within their plasma membrane so as to allow enough cellular space for them to perform their intended duties. All cells require a blood supply to deliver nutriments and oxygen. Many cells exhibit nerve connections to allow communication capability within multi-cellular organisms. Certain cells are able to chatter or signal among themselves and send messages to adjacent and even distant cells to coordinate operational requirements concerned with body or even tumor homeostasis.

Like all biological mechanisms, cells have some sort of electrical signaling process and connections and means to communicate with other cells. Certain cells are connected to adjacent cells of similar type and purpose to allow coordination of their duties and efforts. At the borders of demarcation between different types and families of normal cells there may be signals that maintain separation and cooperation so as not to interfere with each others duties and operations. All functioning organs, muscles, blood vessels or glands are constructed of a variety of cells that together cover all the functions that are required, including sensory and the ability to vary performance.

Cells produce natural, rapid, low voltage, low amperage signals that are discrete and localized. Cellular signals that need to travel long distances use a relay tactic which enlists the cooperation of other cells to help transmit an accurate signal. Most if not all the tiny electrical pulses and codes produced within a cell draw their energy from a specialized chemical or electrochemical process that resides within their surrounding plasma membrane wall and/or within the internal cell itself. The signals are formed from the most fundamental bits of electricity first produced by prehistorical primitive examples of single cell life.

From the general published information regarding paleobiology, paleochemistry and the general literature of ancient times it is believed that over 3.8 billion years ago the first living organisms appeared on a cooling earth in pools of water formed by the reaction of 2 parts hydrogen gas and 1 part oxygen gas. How the available elemental constituents merged and produced the first single cell representation of life can obviously not be fully known. However, present-day biological knowledge is able to present a plausible explanation of how cellular life may have emerged.

To begin with, the early single cell life forms had to function in an atmosphere that did not yet contain oxygen. Such single celled microbes are similar to present day bacterial cells or blue-green algae that do not require oxygen to generate energy. Rather, they used liquid water along with ingested food materials for metabolism to maintain their life. Those early cells are classified as prokaryote because they lacked a central nucleus to carry genetic material. Genetic codes may have existed in the cell wall or cytoplasm of these early prokaryote cells, but that cannot be proven.

Single cell organisms which were located in close proximity of other cells somehow learned to operate in symbiotic ways by capturing or surrounding their food and sometimes sharing it with their neighbors. Those early cells gradually organized themselves into interconnected groups of similar or comparable types of cells to accomplish the required duties and needs to keep the entire group alive, while they floated in the pond together. Specialized cells were organized or enslaved to contribute to the function of these prehistoric clusters or colonies. Some cells in the colony would ward off predators and other specialized cells would work to paddle the colony all in exchange for food and community protection. Cells gradually evolved that could inject a chemical sting or generate an electrical shock to help protect the floating cellular colonies. Today such floating cellular mass might be called "pond scum".

The earth was continuing to bubble and cool down over the centuries as the atmosphere began changing from one abundant in carbon dioxide to one gradually richer in oxygen. Along with these changes came the introduction of other types of life forms and vegetation, including land based life which was also constructed exclusively of cells. Continual but gradual changes in the environment set the stage for differences in how cellular organisms would adapt and use their available resources and habitat, and learn who would be predator or prey.

It is thought that some 3 billion years ago oxygen levels increased in the atmosphere close to the surface of the earth as a result of land based emergence of grasses, bushes, trees and other vegetative species which utilized carbon dioxide and water to make their energy while expelling oxygen as a waste product. This vegetative process is called photosynthesis and is where plants utilize energy from sunlight to create sugars for their own internal cellular requirements. Cellular vegetation grew, seeded and multiplied so that eventually plants had spread away from the pools of water to places farther inland. Eventually vast areas of the earth were covered with a great variety of species of grasses, bushes, trees and vines. Insects which are also composed of cells began to appear and played a symbiotic roll in the reproduction process of green vegetation by pollination and the spreading of seeds over larger areas. The vast amount of vegetation, grasses, trees and green plant life which utilized carbon dioxide and expelled oxygen continued to flourish and gradually alter the earths' atmosphere so it became oxygen rich.

Noteworthy are the contribution of the cyanobacteria (blue-green algae) which produced large amounts of oxygen into the earth's atmosphere starting about 2 billion years ago. This hastened the emergence of the eukaryote cells which could utilize and process oxygen by using its mitochondria organelles for cellular energy. It took a half-billion years for the atmosphere to be changed from a small percentage of oxygen to the modern-day atmospheric composition of 21% oxygen and 78% nitrogen by volume.

With time, perhaps several hundred centuries, this higher concentration of oxygenated atmosphere mixed and spread uniformly over the earth. At the same time microbes and single celled creatures that utilized carbon dioxide for energy were diminishing because they were unable to manufacture cellular energy from the prevailing oxygen levels. Those cells who could not adapt to this shift in atmospheric concentrations perished.

As this was happening, the most primitive prokaryotic cells became largely extinct and were replaced by eukaryotic cells that contained a nucleolus with DNA. The nucleolus featured a large structure which consisted of many loops of chromatin-bound DNA as well as clusters of ribosomal RNA genes. These evolving single-cell structures were continually engaged in high levels of protein synthesis via rRNA. The nucleus and the mitochondria were joined by still other cell components and organelles over succeeding generations to became more complex and sophisticated in embracing the now more abundant oxygen. As the cells changed, they sometimes made genetic mistakes and formed improper structures which multiplied abnormally and often died prematurely or grew into large clusters which died because it could not acquire enough food or oxygen to keep up with its fast growth. Such defective and aberrant ancient cells are thought to be potentially the first evidence of malignancy.

Mitochondria, a cytoplasmic organelle, became responsible for the bulk of energy production in eukaryote cells which featured a nucleus. Mitochondrion organelles are the site at which the electron transport chain and sugar metabolism occurs that results in the manufacturing of useable energy for the cell. It was essential that the newly evolving cells had availability of oxygen because they could no longer live in a carbon dioxide atmosphere and had adapted to their newer method of metabolizing oxygen and sugars as primary substrates. This new cellular life, which exists today, expelled carbon dioxide as its waste product thereby providing the evolving vegetation what they needed.

Examples of these eukaryotic cellular organisms included protozoa, unicellular algae and slime molds. In addition, other uni- and multi-cellular eukaryotic life began flourishing outside of the pond waters, on the shore and inland, such as molds, mushrooms and yeasts.

Fungi likely began appearing 1.3 billion years ago. Plants including cellular aquatic green, red and brown plants evolved about 700 million years ago. Such plant forms took in carbon dioxide and hydrogen to live and expelled oxygen as a waste product. From all of this, a stable oxygen environment evolved and continued on to become the definitive atmosphere of earth. The eukaryote cells that utilized oxygen, became the building blocks of more complex multi-cellular life forms, including those of the kingdom Animalia. These organisms left the water and developed high mobility on land and perfected the practice of hunting, slaying and ingesting other organisms for food as time proceeded on. Early chromosomal and genetic errors created malignant cells in some of the early Animalia which complicated and distorted some biological functions and shortened their life. But at the same time many cells were healthy and performed their duties well and had refined their bio-electric activity and cellular structure. So historically some very old cell designs have continued on and helped carry life functions forward through many, many generations. The great majority of human and animal cells multiplied and organized their internal organelles, reproductive and metabolic parts and systems correctly and survived a normal life span.

In order for the more complex multi-cellular organisms to coordinate their own function, the neuron-cell appeared on the scene to provide a signaling and sensory system that served to help manage its diverse activities. Neuron cells became the first electrical signaling system and evolved an encodement system to manipulate more complex movement, sensing, thinking and chemical processing capability. This was in ancient time, well before humans and dinosaurs existed and when pond vegetation, microbes and neo-fish might have been considered a sort of sophisticated life form. Neurons became the manager and benevolently organized early life forms that were mobile, needed food and had to defend themselves. Over many, many generations, neurons gradually reformed the multi-cellular organism that they were a part of. A neo-brain of neurons formed to compute, remember and evaluate, and produced its own sensors such as eyes and a measurable sense of touch to allow it to guide the life of all the cells that had become part of it.

To grasp how this happened, imagine how it might have been during that pre-history period of time some 1 billion years ago, when the neuron-cells actually organized themselves into a communication system for multicellular creatures of the era. Gradually, the most sophisticated mixed cell groups floated as a large mass on water and organized themselves by specialty cell function. Some cells digested food, others protected the colony by shocking and stinging enemies, while still other cells were able to locomote the entire floating organism with oar-like flagella beating upon the water.

At first, these cellular communities lacked any method to coordinate themselves. They needed a command and communication system. To accomplish this the amazing neurons had the capability to generate tiny variable electrical signals and send those via nerves to distant areas of those earlier multicellular organisms as communication. Certain kinds of cells also became more complex and developed the capability to interpret the neuron signals and to act on them. In addition the more sophisticated cells were able to use neurons to send status information and other replies back to the neo-brain, which was made up of clusters of neurons and supporting glial cells. The neo-brain became a place where instincts and experience were resolved and actions planned and directed.

This was facilitated by the evolvement of simple sensors for the central neo-brain that made decisions and provided instructions to locomote, protect, and find food. This was the beginning whereby eventually all species of Animalia became dependent on the capabilities of their neuron cells. Messages were relayed and sent over the colony by strings of primitive nerves which utilized strings of neurons to generate and transfer encoded electrical instructions to functioning aspects of specialized organs that were part of the gradually advancing multi-cellular organism.

As time went on, neurons continued to organize and sophisticate living organisms and came to cooperatively operate the various systems that maintained homeostasis of all creatures, later to include homo sapiens. It became obvious that the neuron codes had to be understood by many other kind of cells that in themselves had only to understand the message and act. So gradually all cells developed some sort of electrical communication system to coordinate themselves and their adjacent cells by being able to communicate and cause harmonious actions that were a benefit for the entire multi-cellular organism. Sensory cellular systems were tasked with sending information to the neo brain to provide status information from outside the multi-cellular organism as well as from the inside.

With time came the appearance of animals and man-like organisms more complex than any other living thing the earth had seen. These were able to operate sensors for taste, smell, vision, hearing and touching that allowed them to understand, operate and live within their environment more successfully than all other earlier examples of life. Many varieties of animal species began to roam the earth in herds or establish themselves in nests and caves to co-exist and to hunt and defend themselves. Homo sapiens, in particular, were able to discover, invent and to gradually build a remarkable life and habitat that far exceeded any accomplishments of other members of the Animalia kingdom. Primates, reptiles and insects, for example, still exist as they have since their origin as a species.

On the other hand, homo sapiens have progressed and advanced steadily as a species and built the world we live in today.

Man-like species seem to have appeared about 7 million years ago, but more modern man likely evolved on earth only around 100,000 years ago. Modern man had a larger, more creative brain and more agile hands and fingers which allowed him to manipulate objects and create tools. Only about 50,000 years ago a chance variation in the human genetic coding likely provided man with the gift of language and still higher cognitive thinking. What man could think up, he learned to build by trial and error. Verbal communication and cooperation with his clansmen allowed for a organized effort. Mankind began to colonize as a people and to explore the vast horizons in which they lived, roaming over the vast distances of earth. They learned how to cooperate, find food and hunt, discover fire, build shelters and care for their offspring over long periods of time.

With the advancement of mankind came an ever more sophisticated cellular communication system over the entire being including from cell to cell and from cellular system to other cellular systems. Cells had to have a way to transfer signals not only between adjacent cells but inside the cell itself to operate its own individual metabolism and repair operations. To do that, the cell utilized chemicals and ions of sodium, potassium, magnesium and calcium to electro-chemically generate an electrical signal in the form of a spark. So chemical processes begot electrical signaling. The spark shape, amplitude and frequency created the communication encodement system for all kinds of cells that operated everything within the human body. Less sophisticated but similar cellular communication systems were found in the higher order animals. The intellectual capabilities of human brains were vastly superior to that of any faculties found in animals. The ability to manipulate hands and fingers provided mankind with the means and dexterity to build and manipulate what he could think of in his mind.

Cells are attached to one another for the purpose of maintaining structural integrity and to facilitate communication between cells. Some sort of cytoskeleton provided cellular shape and strength to every cell. Connections through the cell walls serve as structural methods to both attach to adjacent cells and to allow communication between those connected cells. The operative connections between cells can take several forms. They can be laced together with fibrous strands, gap junctions or ion channel ports which are riveted together. Additionally, other tactics for joining cells exist as tight junctional contacts. It is the objective of cells to have communication mechanisms between all cell walls that touch neighboring or adjacent cells of like-type cells. Otherwise, when a border exists between entirely diverse cell types there may be little communication. Instead the diverse cellular based vital-organs, glands or muscles operate via a two-way nerve networks to and from the brain for exchange of information and coordination of all activity. Neuron signal sets are stored in brain structures to serve as readily available information for body homeostasis. Strings of neurons within nerves provided two-way communication between organs, muscles, glands, sensors and all other body components that are part of the higher order mammals including man.

Since the 1970s, Eleanor Schuler, one of the inventors of the present application, has studied the bio-medical literature and developed the concepts of how neuron-cells and other cells encode and transmit two-way information. Schuler's inventions and advancement in computer systems and electronics made it possible to actually record and see neuron cellular signals accurately. As a result, a number of U.S. patent applications were filed and some have been issued to establish and demonstrate how neurons communicate and regulate vital organs, muscles and glands and maintain body homeostasis. Noteworthy is that neurons use a number of different signaling patterns to elicit variations in organ system performance, such as a faster or slower heartbeat or respiration frequency and depth of inhalation. Schuler et al have been granted the following patents: U.S. Pat. Nos. 6,633,779; 6,937,903; 6,681,136; 6,957,106; 7,058,446; 6,775,573; 7,062,324 and 7,308,302, among others. The disclosures of these patents are incorporated herein by reference.

In addition, Schuler et al have performed studies with laboratory animals to elucidate and establish that neuron-cell signals can be recorded, stored in computer memory and be re-transmitted into nerves to operate vital organs, muscles and critical systems, such as the respiratory function. Such studies have been conducted in vivo with several kinds of laboratory animals.

Many cells are involved in receiving communications and also can send signals themselves. However, those that understand that cellular signaling exists might well believe that most of it is done chemically, and perhaps only within the cell itself. Most people acknowledge that there is electrical signaling in the brain. They even believe that there is a great amount of signaling between many brain structures. Usually those who advance into neuroscience studies recognize that nerve communication is at work where neurons are involved, but they will only partially understand that mechanism. On the other hand, neuroscientists that have experience in recording nerve signals from simple animals do not know how to store the signals in a scientific computer system where it would be available for re-transmission into a damaged or severed nerve to make something happen. Electrical signaling in nerves or cells is still an emerging field.

Every biological process is also an electrical process. Cells that have electrical signaling capability can communicate at a minimum within a single cell or a small group of similar cells. Some signals merely turn on internal processes having to do with reproduction or metabolism. While functional cell clusters have erected a network for sending signals among themselves. Cell clusters that make up functional systems are also connected to nerves that both bring information from the brain but allow for sending status information back to the brain, which allows for adjustment in the operating signals.

There are no medical technologies in commercial use that record, store, reprogram and transmit ultra-low voltage cellular signals that could affect cellular electrical communication and its associated performance.

Living cancer cells also have a rigorous communication system and a method to generate an outer membrane electrical charge as part of their camouflage from attack by the human or animal immune system. They have many characteristics that predominate in normal non-malignant cells of every type, especially having to do with metabolic processes.

One of the things that make cancer cells so lethal is that they can reproduce themselves continuously and establish significant clusters of malignancy. Normal cells can only reproduce a certain limited number of times, usually not more than about 70 times in their lifetime.

Many cancer cells have malformed chromosomes and certain aberrant genetic morphology that contribute to their invasive and aggressive characteristics. Entire chromosome mutations may also contain thousands of genes, some of which can also be severely abnormal, missing and/or scrambled as to their proper location. Some defective budding cancer cells may be so malformed that they can not live and therefore, do die. But if only a single cancer cell survives intact it can proceed to reproduce to form a malignant tumor. If such a single new cancer cell can stabilize itself and become viable it will start dividing and eventually generate a multicellular malignant tumor—all from a single cell.

Cancer cells serve no good purpose to the body as a whole. Cancer cells are the natural enemy of all the other cells and structures that make up the human or animal body. Although cancer is generally considered primarily a genetic disease, evidence now leads to the malformed chromosome theory. Noteworthy is that genetic material resides on chromosomes. Cancers also can arise from a triggering event such as an overdose of sunlight, or inhalation of known initiating chemical influences such as tobacco or asbestos. It has also been proven that even viruses and other microbials can be causative for initiating and propelling cancer formation.

Defective chromosomal and genetic forces which are inherited do a lot of mischief and severely threaten life and account for much of cancer's morbidity and mortality in humans and animals. Unfortunately, present day medical treatments, as remarkably successful as they are, are simply not always good enough. Part of the practical problem is that it is difficult to detect most early stage malignancies. When cancer is eventually recognized it may have extended into nearby tissues, bones, blood vessels, lymphoid systems and organs in an already progressing unpleasant metastatic process. Many cancer patients don't come to in the clinician's office until serious tumor symptoms are at hand. Physical examination, history taking, X-ray and CT scan often provide the initial information and clues as to the location and staging of a malignant tumor. Further evaluation can be accomplished by exploratory surgery, pathology studies, MRI and/or PET scans. Bone scans are an important test. Biopsy to collect a sample of a suspected tumor and microscopic studies by a pathologist are utilized to identify the species and to grade and stage any cancerous tumors. Blood tests for tumor markers is a growing diagnostic tool. Out of range values from normal or specialized blood tests add to the information. Today there is a major quest to identify all cancer sites and plan a treatment regime for every patient. The foundation of present-day treatments embrace surgery, radiation and chemotherapy.

It is well known that cancer cells have escaped the control mechanisms that regulate growth. Cancer cells have a ravenous appetite for glucose and have chromosomal imbalances involving networks of damaged or aberrant genes. Pathology studies often show multiple or distorted nuclei formations. The environment for cancer formation may feature an inflammatory process in which cancers can thrive. Tumor clusters of cancer cells can shed some of their cells to allow a metastatic process to seed new tumors in predictably preferred locations throughout the body. It is also possible that the shed tumor cells may also be able to communicate with the primary cancer site as it launches its journey to establish a new tumor colony. Cancer clusters can send signals that encourage the formation of new and larger blood vessels to feed an enlarging tumor mass.

Cancer cells exhibit altered electrochemical properties and variant distribution of their electrical signals from those of normal tissues. Cancer cell walls move nutrients differently than normal cells and use their outer glycocalyx as a protective barrier to discourage attack by the bodies immune system. The glycocalyx is a carbohydrate-enriched cell wall which is the outermost surface with a strong negative electrical charge.

Cancer cells exhibit lower impedance and electrical membrane potential than healthy cells. The malignant cell has higher levels of sodium which contributes to the electrochemical ability to generate internal signals. Cellular electrical abnormalities likely may be the basis of the rapid cancer reproduction and the root of its aggressiveness. Likely both the plasma membrane charge and the internal electrical metabolic and reproductive signaling carry the instructions that drive the relentless spread of cancer clusters. The cancer cell features a well established electrical constant which is unlike healthy cells. Therefore a tactic that would alter the tissue electrical encodement of a cancer cluster is expected to interfere with the internal metabolic process and reproduction, as well as its resistance to attack by the immune system. This electrical characteristic is dependent on electrophilic compounds associated with the cell membrane wall and the availability of ions and electromagnetic forces in the extracellular spaces around the cell. Additionally, the water content, oxygen levels, minerals, pH, and the organization of the plasma membrane all interplay with the way the cancer signals.

Destroying the cancer cell electrical system is the goal of the present invention. Ruination of the electrical properties of the cell can be expected to prevent mitosis, disturb metabolic processes, scramble internal cell communication as well as signaling to adjacent cancer cells. With damage to the internal communication processes the cellular processes that use oxygen, glucose, potassium, sodium, calcium, magnesium and other minerals and chemicals will be disturbed. Transport of anticipated nutrients to and through the cell interior will be in confusion as to intercellular workings. Finally the loss of its electrical system will no doubt disturb the electrochemical reactions that occur within the individual cancer. The invention's interclusio and mortifier treatment signals cascade the tumor towards catastrophic cellular systems failure.

SUMMARY OF THE INVENTION

The invention provides a method and system for severely disabling or destroying cancer cells by interfering-with or shutting-off the cellular electrical and communication systems. The treatment method is also designed to interfere and reverse the plasma membrane cell wall glycocalyx electrical charge from negative to positive by injecting ions of potassium, sodium, magnesium or calcium into the plasma membrane by means of the imulus treatment device to disturb the ionic or molecular pump balance. On the other hand, if it is desired to alter the glycocalyx so that it is more or less negative, the ions of chlorides, sulfates or phosphates may be used.

The treatment technology protects or at least limits damage of adjacent or neighboring non-cancerous, normal, and healthy cells. Barriers or shields to the electrical treatment signals may be utilized to protect sensitive structures. The treatment commences by recording the electrical signals of a cancer cell or group of cancer cells and storing such signals in a scientific computer system. Such cancer cell signals are compared to an existing cancer signal library to determine if there is an appropriate treatment signal package available to use as treatment. If not, the recorded signal is evaluated and altered by reprogramming within the scientific computer system to confound the electrical cellular apparatus when the codes are transmitted into the cancer cell cluster.

A scientific computer system is used to record and store within a computer processor the resident electrical signals found in cancer cells. Stored data banks of cancer signals recorded from laboratory animals or from animal or human patients are available to study and compare by cancer researchers. Treatment signals likewise are also stored in a computer data base for study and as a contribution to developing treatment modalities in cancer patients. The cellular signals are analog in nature and are reprogrammed within the processor to serve as confounding signals and then are saved in another data base memory for later transmission into cancer cells as medical therapy. The invention shuts down or damages the natural electrical signals and the affected processes of cancer cells so as to cause cell death.

BRIEF DESCRIPTION OF THE DRAWINGS

The invention is described in greater detail in the following description of examples embodying the best mode of the invention, taken in conjunction with the drawing figures, in which.

DESCRIPTION OF THE INVENTION

The invention consists of a method and system to treat cancer with a hybrid scientific computer system composed of components to acquire, display, document and store cancer cell electrical activity and then to record and program or re-program the cellular electrical activity. Finally treatment signals are transmitted into selected cancer cell tumor clusters to damage and terminate the cancer.

The objective of the invention is to disable or destroy cancer cells by interfering with or shutting off the cancer cellular electrical system without impacting healthy cells. The treatment is performed in vivo. The resident electrical signals of a cancer cell or group of cancer cells are recorded, stored and displayed in the computer system.

Once the cancer cells/cluster or tumor is analyzed appropriate action is taken to program or reprogram the resident electrical signal(s). The computer system is utilized to affect electrical stimuli to confound and treat the cancer electrical circuits by transmitting the properly programmed encodement into the cancer cell or cluster, without seriously negatively impacting adjacent or neighboring healthy cells.

Cancer cell resident electrical signals are analog in nature and to be recorded, the computer system must utilize an analog to digital (A-D) converted as the signal receiving entry point to the system. All cancer cells utilize and send and receive analog electrical signals. The cancer cell signals cannot be accurately recorded with a direct digital system. Once created, any cancer cellular treatment signal, i.e., a confounding electrical signal, must be reprogrammed by a digital to analog (D-A) converted before it is sent back into the cancer to confuse or confound its cellular electrical system.

Figure 1:
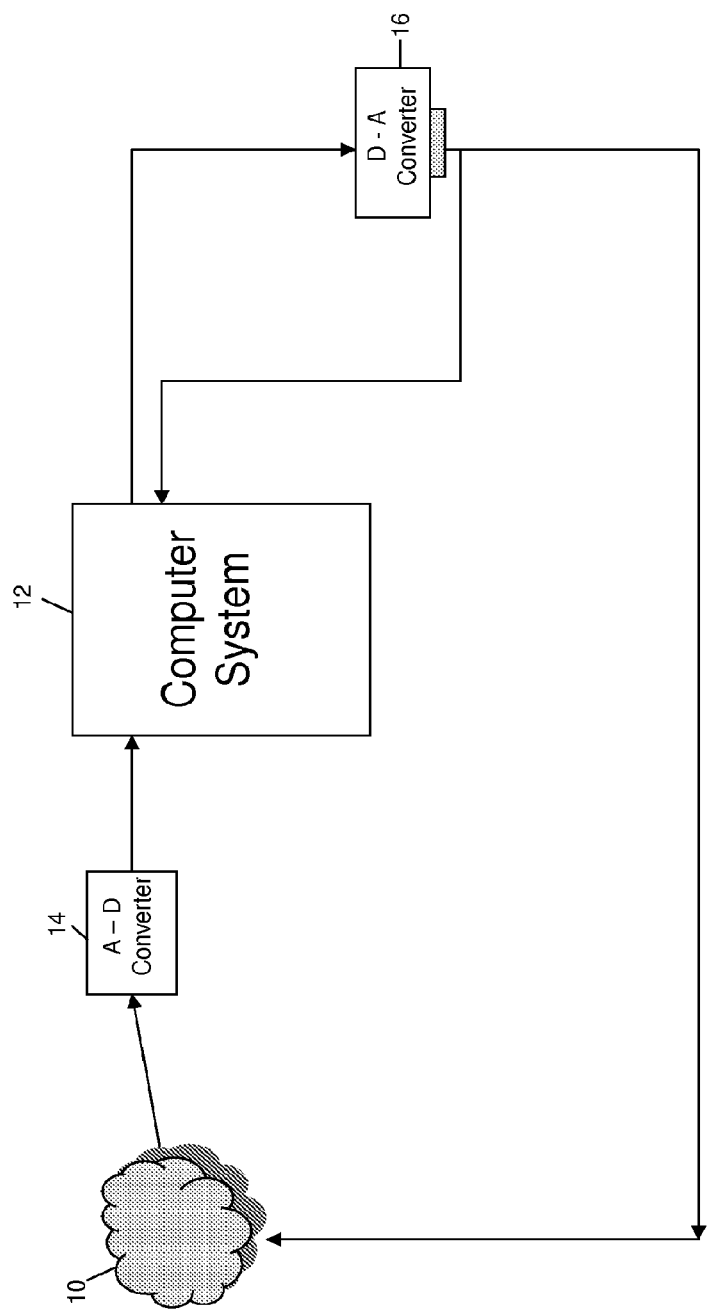
FIG. 1 is a schematic illustration of the system according to the invention for determining a resident electrical signal found in cancer, creating a confounding electrical signal and applying the signal to the cancer.

A cancer cell cluster or tumor is illustrated at 10 in FIG. 1. By means of an imulus or other probe, the resident electrical signal or signals of the cancer are then provided to a computer system 12 for storing and processing. Typically, the computer system 12 is digital, and in order to accept the electrical signals from the tumor 10, an analog to digital converter 14 is used. If the computer system 12 employed includes an embedded analog to digital converter, the converter 14 can be omitted.

It is the computer system 12 in which all of the processing, analysis and generation of confounding electrical signals occurs. In order to treat the tumor 10, the confounding electrical signals are applied directly to the tumor 10 via an imulus or probe after conversion to analog state by a digital to analog converter 16.

The technical approach is to initially develop a number of cancer cell resident electrical signals for different species of cancer and perfect reprogrammed confounding type signals. The user then sorts and reprograms the natural signals of the cancer cell and tinkers with the electrical signatures and coding to finally select appropriate treatment electrical signals, also known as confounding electrical signals. This is followed by devising a library/data-base of treatment signals. The collection of treatment signals may be cataloged as to the species of cancer and anatomical location. During treatment of a cancer the first step is to identify the species of cancer and then select the proper confounding signal with which treatment will begin. Once the treatment team knows the species such as carcinoma or sarcoma they select from the computerized library/data-base the most appropriate treatment signal. There are approximately about a total of 200 cancer species in existence. Ultimately the treatment library will be composed of at least as many definitive cancer confounding, interclusio or mortifier signals. Carcinoma species is the most common cancer and likely represents something like 50% of all cancerous tumors throughout the body.

Once the cancer cell locations in a patient have been identified, the cancer cellular electrical activity has been recorded and analyzed, and an appropriate response has been determined, the medical staff can develop and initiate a treatment protocol. The protocol will follow established medical procedures with the main objective of applying the proper signals and appropriate electrical energy to the cancerous cells to cause apoptosis. The computer system 12 contains a low voltage and amperage power supply to ensure the correct voltage and amperage is delivered to the cancerous cells. The electrical energy delivered is less than 1 volt and less than 10 millionths of an amp for a pulsed application on the cancer over a few seconds. The treatment may be repeated. The range of electrical treatment may span upwards of 2 volts and 70 micro amps and as low as one-tenth of a volt or possibly even lower at 2 microamps or even lower into the picoamp range. The treatment time may extend up to 4 minutes or more and is repeatable over days if required. The treatment signals in the form of an electrical signal will have a definable shape and be encoded to confound the natural electrical activity found in the cancer cell plasma membrane wall and within the very interior of the cell proper. With the use of the proper code to shut off cellular electricity, the result is apoptosis of the cancer. Cancer death can begin in less than an hour once its metabolic processes are shut-down. Cell death actually may occur in less than 10 minutes as a human brain cells do when blood circulation or electrical signals are turned off. Natural resuscitation of the cancer cell may be possible if the confounding electrical signal treatment is too brief or incomplete. Otherwise irreversible biological decay will set in as long as the cellular process has been severely damaged by the treatment signals. The body immune system is expected to consume the dead or dying cancer as soon as the outer cell membrane negative electric charge is off or markedly diminished. It is the strong negative outer electrical charge of the cancer cell membrane glycocalyx that keeps the immune cells from attacking since they too are negatively charged and would be repelled from one another. Normal cells have outer coat charges that are usually positive and are therefore accessible to the negatively charged immune system cells.

Figure 2:
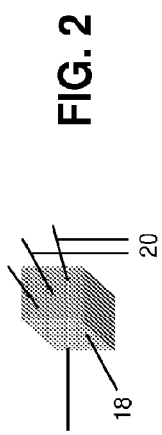
FIG. 2 is a schematic illustration of an imulus treatment tip or probe having a plurality of nanotubes or nanowires.

Treatment is done with a small cable of total diameter no more than a wooden match stick. The imulus or treatment contact unit 18, as shown schematically in FIG. 2, is small but contains hundreds or thousands of carbon nanotubes 20. The nanotubes may be hollow or partitioned. In addition they may be coated with a metal deposition, or chemical that interferes with the glycocalyx strong negative electrical charge. The carbon nonotubes equipped imulus 18 will appear under a microscope like a hair brush. Each nano fiber tube is about one-ten-thousandths of a human hair in diameter. The imulus 18 can be used to both record and apply the treatment signal and may be of different sizes to fit the various cancer clusters. The physical approach to the cancer can be guided by fluoroscopy or other visualization apparatus or system to insure that the treatment is applied properly and completely and is directed at the correct target.

The imulus 18 is positioned to make contact with the tumor as the primary junction between the computer system 12 and the malignant cellular tumor 10 which is to be treated. Some modified nano carbon tubes may also act like an antenna and only need to be in close proximity of the malignancy to send in the interclusio or impulses mortifier codes, Insertable links, implantable antennas and contact pads or implacable treatment needles of carbon or metal can be in the arsenal of imulus attachments, among others.

It is preferred that analog computers are used that are as sensitive and able to record the cancer electrical signals as required. As analog computer developments advance they may be more suitable and be the system of choice in destroying cancer cell life. Otherwise the system as illustrated can utilize A-D and D-A converters 14, 16 interfaced with a digital processor in the computer system 12 using appropriate software to control confounding signals.

The main treatment quest consists of locating all of the cancer islands and clusters for treatment. Signals to shut down the cancer must affect every malignant cell at a given site. Communication can travel through portions or layers of tumor cells, traveling from cell to cell. Therefore moving the imulus around the tumor 10 will be necessary to make certain that every cellular communication system present within the malignancy is disabled or destroyed.

While the preferred signal handling system embodiment to destroy cancer cells is a full analog technology, the current state of computer systems is not able to deliver such a scientific computer that would work at the extremely ultra-low voltages and at the speed required to capture and record the natural signals of cancers. Therefore FIG. 1 outlines the requirements for a hybrid system to process cancer treatment codes. The system of the invention uses a hybrid analog/digital computerized system which requires at its entry an A-D converter 14 of high sensitivity to record the exclusively analog cellular signals of cancers. Secondly, the signal has to be transferred into a digital processor in the computer system 12 where it can be stored and reprogrammed to confound the natural cellular signals and control any power supply required.

The computer system 12 includes several components. First, it must have a typical laptop or desktop computer for control, data acquisition, programming and application of treatment. It must allow for storage of ambient and environmental signals as well as potentially interfering biological noise so that the treatment or confounding electrical signals can be as pure as possible. LabVIEW Graphical Software provided by National Instruments Corporation of Austin, Tex. is particularly suitable for handling the graphical aspects of the invention. Insofar as hardware, the National Instruments CompactRIO Control and Acquisition System can be used, or any other similar system of National Instruments or others can be used.

The following definitions apply to the terminology of the present application:

Iqniculus signals: The intrinsic operational cellular electrical communication signal, also known as a resident electrical signal, of a cancer cell. Such codes are recorded, studied and re-programmed to develop treatment signals. Interclusio treatment codes: A treatment communication signal that can stop, confound or pause cancer cell's electrical activity, also known as one form of a confounding electrical signal. Such signal may be pulsed or applied for a calculated period of time to at least damage the cancer cell electrical system to the extent that places the cell on a downward slope toward apoptosis. Used where the malignancy is close to other sensitive structures.

Mortifier Impulus treatment codes: Coded signals that are programmed to cause fatal and irreversible cell death by rapidly destroying the signaling system of a cancer cell cluster to insure the death of the tumor, another form of confounding electrical signal.

Imulus: A treatment tip which is applied directly to a cancer tumor and carries electrical treatment signals via carbon nanotubes or very small metal nanowires. Leads from the scientific computer system 12 connect to the imulus 18. Up to hundreds to thousands of carbon nanotubes 20 may be emplaced on the imulus to transmit the proper treatment code. The imulus may carry and release chemicals and ions into the cell cluster membranes and also inject anticancer signals and ions into the cell(s) proper.

Carbon nanotube: Tiny hollow carbon filaments that are about one ten-thousandths the diameter of a human hair. They can be 100 times stronger than steel and able to conduct electricity better than copper. They are meant to touch or pierce the plasma membrane of cancer cells to transmit the treatment signal into the cell processes. As part of their function they can also carry positive or negative ions in the hollow of the nanotube to treat the cell wall glycocalyx to reverse its electrical charge. They are a component of the imulus.

LabVIEW Digital Computer Software: Software manufactured by National Instruments, Version 8 or higher, which is a graphical programming language that uses icons to create applications. It can assimilate libraries of signals and sort to help arrive at the desired final treatment signal. It has capability for processing high speed ultra-low voltage biological signals. This software coupled with the scientific computer system 12 will communicate, record, reprogram and transmit altered cancer cell signals, the confounding electrical signals, designed to damage or destroy cancerous tumors.

Various features of the invention have been shown and described above. However, it must be understood that what is described herein does not limit but merely illustrates the invention. Various changes can be made to the invention without departing from the spirit thereof or scope of the following claims.

What is claimed is:

1. A method of treating cancer by causing apoptosis, where the cancer is one of known species of malignant cells, comprising the steps of
   a. determining the specie of the cancer, and
   b. applying a confounding electrical signal to the cancer to cause apoptosis.

2. The method according to claim 1, in which the confounding electrical signal is selected from a database of confounding electrical signals.

3. The method according to claim 1, in which the confounding electrical signal is applied with a voltage less than about 2 volts.

4. The method according to claim 3, in which the voltage is greater than about 0.1 volt.

5. The method according to claim 3, in which the confounding electrical signal is applied with a current less than about 70 micro amps.

6. The method according to claim 5, in which the current is greater than about 2 micro amps.

7. The method according to claim 1, in which the step of applying has a duration of up to about 4 minutes.

8. The method according to claim 1, in which the step of applying is with an imulus.

9. The method according to claim 8, in which the imulus comprises a plurality of nanotubes.

10. The method according to claim 1, including the step, after step a and before step b, of determining a resident electrical signal found in the specie of cancer.

11. The method according to claim 10, in which the step of determining a resident electrical signal is with an imulus.

* * * * *